United States Patent [19]

Buchel et al.

[11] 4,117,142
[45] Sep. 26, 1978

[54] DISUBSTITUTED TRIPHENYLMETHYLIMIDAZOLES FOR TREATING MYCOTIC INFECTIONS

[75] Inventors: Karl Heinz Büchel; Erik Regel; Manfred Plempel, all of Wuppertal, Germany

[73] Assignee: Bayer Aktiengesellschaft, Germany

[21] Appl. No.: 726,568

[22] Filed: Sep. 27, 1976

Related U.S. Application Data

[60] Continuation of Ser. No. 501,167, Aug. 28, 1974, abandoned, which is a division of Ser. No. 339,430, Mar. 8, 1973.

[30] Foreign Application Priority Data

Mar. 22, 1972 [DE] Fed. Rep. of Germany ....... 2213863

[51] Int. Cl.$^2$ .......................................... A61K 31/415
[52] U.S. Cl. .................................................. 424/273 R
[58] Field of Search ......................................... 424/273

[56] References Cited

U.S. PATENT DOCUMENTS

| 3,321,366 | 5/1967 | Mossell et al. | 424/273 |
| 3,691,192 | 9/1972 | Buchel et al. | 424/273 |
| 3,711,498 | 1/1973 | Buchel et al. | 424/273 |

FOREIGN PATENT DOCUMENTS

| 1,581,925 | 9/1969 | France | 424/273 |
| 1,600,990 | 9/1970 | France | 424/273 |
| 1,170,188 | 11/1969 | United Kingdom | 424/273 |

*Primary Examiner*—Jerome D. Goldberg
*Attorney, Agent, or Firm*—Jacobs & Jacobs

[57] ABSTRACT

Imidazoles of the formula

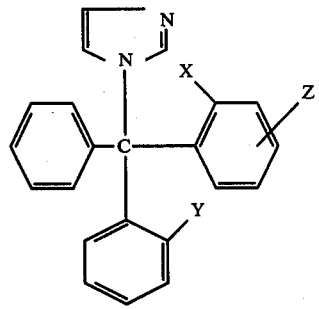

and pharmaceutically acceptable nontoxic salts thereof, wherein
 X is methyl or chloro,
 Y is methyl or chloro, or, when Z is methyl or chloro, Y is hydrogen, and
 Z is methyl or chloro, or, when Y is methyl or chloro, Z is hydrogen, are useful as antimycotics for the treatment of mycotic infections in humans and animals. The imidazoles may be produced by reacting the corresponding triphenylmethylcarbinol with a brominating or chlorinating agent and thereafter reacting the resultant triphenylmethyl halide, either with or without isolation, with imidazole in the presence or absence of an acid-binding agent, or they may be prepared by reacting a triphenylmethyl halide with imidazole, either in the presence or absence of an acid-binding agent.

6 Claims, No Drawings

DISUBSTITUTED TRIPHENYLMETHYLMIDAZOLES FOR TREATING MYCOTIC INFECTIONS

CROSS-REFERENCE

This is a continuation of Ser. No. 501,167, now abandoned filed Aug. 28, 1974 which itself is a divisional of Ser. No. 339,430 filed Mar. 8, 1973.

The present invention relates to new disubstituted triphenylmethylimidazoles, several processes for their production, pharmaceutical compositions utilizing said compounds as the active agent, and methods of treating mycotic infections in humans and animals.

It has already been disclosed that some N-tritylimidazoles are active against plant-pathogenic fungi (U.S. Pat. No. 3,321,366). It has furthermore been disclosed that some N-tritylimidazoles are active against human-pathogenic fungi such as epidermatophytes and other dermatophytes as well as blastomyces and biphase fungi (Belgian Pat. No. 720,801; U.S. Pat. Nos. 3,665,899; 3,665,900; 3,657,442; 3,657,445; 3,658,956; 3,660,576; and 3,660,577). The compounds of the present invention represent an advance in the art over said known compounds and are superior compounds for oral administration.

Disubstituted triphenylmethylimidazoles of the formula

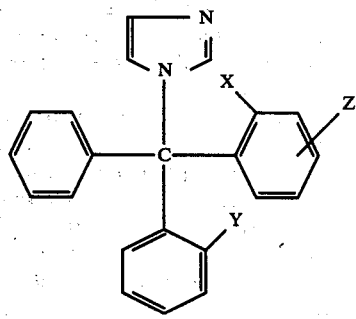

and pharmaceutically acceptable nontoxic salts thereof, wherein
X is methyl or chloro,
Y is methyl or chloro, or, when Z is methyl or chloro, Y is hydrogen, and
Z is methyl or chloro, or, when Y is methyl or chloro, Z is hydrogen,
display strong antimycotic activity.

The disubstituted triphenylmethylimidazoles of the formula (I) and their salts can be produced by reacting
(a) a triphenylmethylcarbinol of the formula (II)

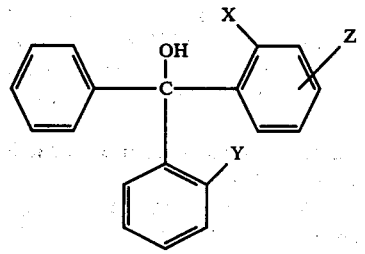

wherein
X, Y and Z are as above defined, with a brominating or chlorinating agent and thereafter reacting the resulting triphenylmethyl halide optionally after its isolation, with imidazole, optionally in the presence of an acid-binding agent; or (b) a triphenylmethyl halide of the formula (III)

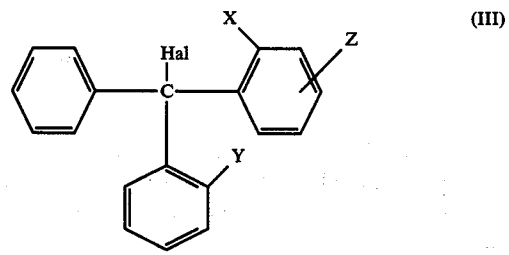

wherein
Hal is bromine or chlorine, and
X, Y and Z are as above defined,
with imidazole, optionally in the presence of an acid-binding agent. The salts are prepared by conventional techniques wherein the free base is reacted with the appropriate acid to form the desired salt.

Surprisingly, the disubstituted triphenylmethylimidazoles according to the present invention exhibit good antimycotic activity together with good toleration.

If 2,6-dichlorophenyl-diphenylmethylcarbinol and imidazole are used as the starting substances, the course of the reaction can be represented by the following equation:

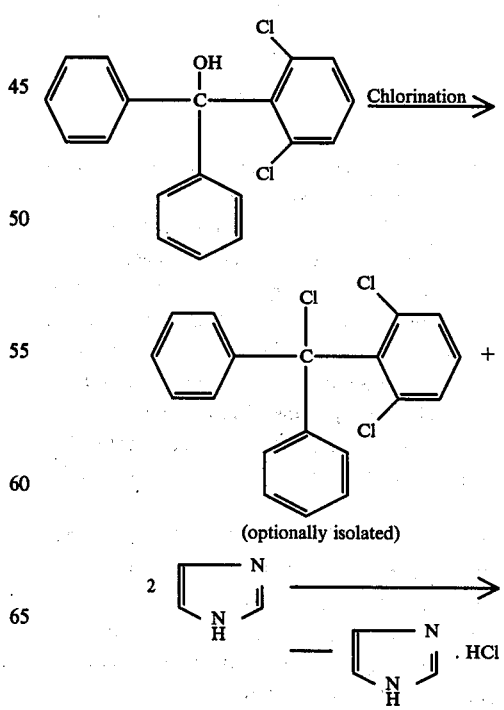

-continued

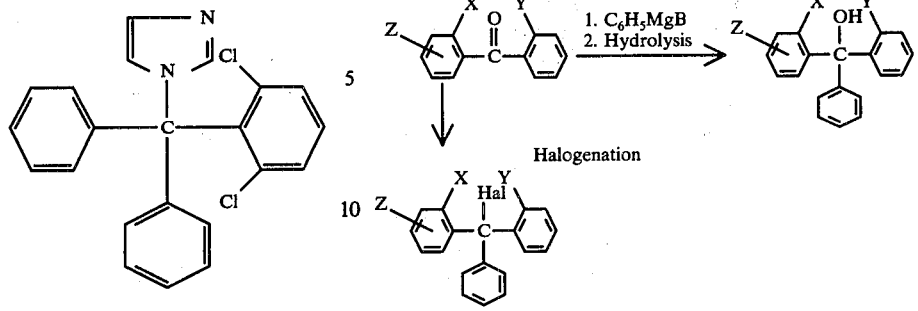

Halogenation

If 2,6-dichlorophenyl-diphenylmethyl chloride and imidazole are used as the starting substances, the course of the reaction can be represented by the following equation:

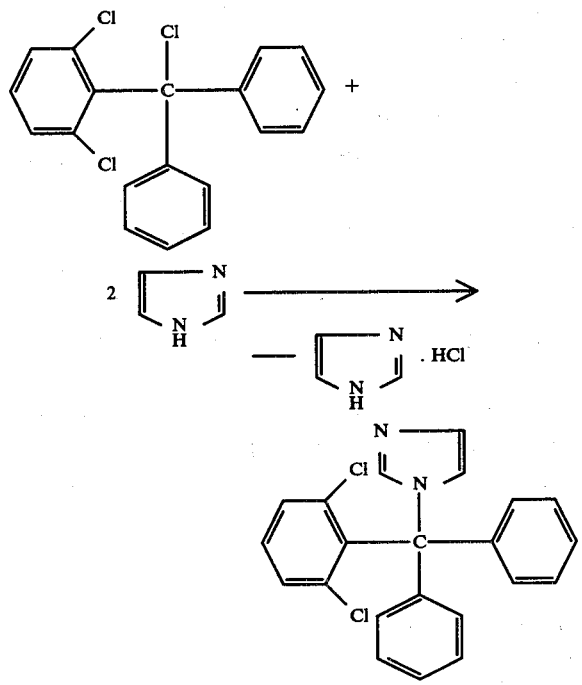

The starting compounds are unambiguously defined by the formulae II and III. As examples there may be mentioned: 1-(2,3-dimethylphenyl-diphenyl)-methyl chloride, 1-(2,4-dimethylphenyl-diphenyl)-methyl bromide, 1-(2,5-dimethylphenyl-diphenyl)-methyl chloride, 1-(4-chloro-2-methylphenyl-diphenyl)-methyl chloride, 1-(2,3-dichlorophenyl-diphenyl)-methyl bromide, 1-(2,6-dichlorophenyl-diphenyl)-methyl chloride, 1-(2-methylphenyl-2'-methylphenyl-phenyl)-methyl chloride, 1-(2-chlorophenyl-2'-chlorophenyl-phenyl)-methyl chloride as well as the corresponding triphenyl-methylcarbinols.

The triphenylmethylcarbinols and trityl halides used as starting materials are known or can be manufactured in a known manner from the corresponding diphenylketones by reaction with phenylmagnesium bromide, hydrolysis and, optionally, subsequent halogenation in accordance with the following equation:

Suitable pharmaceutically acceptable nontoxic salts of the new disubstituted triphenylmethylimidazoles are those obtained from physiologically tolerated inorganic and organic acids. Examples of such acids are the hydrogen halide acids, such as, for example, hydrochloric acid, hydrobromic acid, phosphoric acid, sulphonic acid, for example naphthalenedisulphonic acid, monocarboxylic and dicarboxylic acids and hydroxycarboxylic acids, for example tartaric acid, lactic acid, malic acid, citric acid, salicylic acid, sorbic acid, or ascorbic acid.

Possible diluents for the process according to the invention (Variants (a) and (b)) are all inert aprotic polar organic solvents. These preferably include lower alkyl nitriles, for example acetonitrile; lower dialkylformamides, for example dimethylformamide; dimethylsulphoxide, lower alkyl ketones, such as, for example, acetone and diethyl ketone and hexamethylphosphoric acid amide and nitromethane.

All customary acid-binding agents can be used as acid-binding agents in the reaction of the trityl halides with imidazole. These agents preferably include: inorganic bases such as alkali metal hydroxides, alkali metal carbonates, alkaline earth metal hydroxides, alkaline earth metal carbonates and organic bases such as amines, especially tertiary amines and heterocyclic bases. As examples of particularly suitable compounds there may be mentioned: sodium hydroxide, calcium hydroxide, calcium carbonate, potassium carbonate, methylethylamine, ethyldicyclohexylamine, triethylamine, piperidine, pyridine and lutedine.

In Process Variants (a) and (b) the reaction temperatures can be varied over a substantial range. In general the reaction is carried out at between about 20° and about 150° C, preferably between 60° and 100° C.

The reaction can be carried out under normal pressure but also at elevated pressure. In general, normal pressure is used.

The bromination or chlorination of the carbinols of the formula II is carried out in a known manner with the customary halogenating agents, for example hydrogen chloride, thionyl chloride, thionyl bromide, phosphoryl chloride, acetyl chloride or acetyl bromide. The isolation of the triphenylmethyl halides formed can be effected in the usual form.

In carrying out the process according to the invention (Variants (a) and (b)) the starting compound of the formulae II or III, the halogenating agent (if required), the imidazole and the acid-binding agent are preferably employed in approximately molar amounts. If an excess of imidazole is employed as the acid-binding agent, preferably about 2 mols of imidazole are used per mol of trityl component in the process according to the invention.

For the isolation of the compounds according to the invention of the formula I, which is effected according to known methods, for example the solvent is removed by distillation and the residue left is purified in the customary manner by recrystallization. In some cases it is advisable to manufacture the salt according to customary methods, for example by passing in hydrogen chloride gas, without isolating the bases which are at times oily or, if the free base is desired, to convert the bases into salts and subsequently to liberate the bases again in a known manner. In this way, the free bases of the formula I can be obtained in good purity.

The following are new compounds according to the present invention:

TABLE 1

(1) 1-(2,3-Dimethylphenyl-diphenyl)-methyl-imidazole
(2) 1-(2,4-Dimethylphenyl-diphenyl)-methyl-imidazole
(3) 1-(2,5-Dimethylphenyl-diphenyl)-methyl-imidazole
(4) 1-(2-Methyl-4-chlorophenyl-diphenyl)-methyl-imidazole
(5) 1-(2-Chloro-4-methylphenyl-diphenyl)-methyl-imidazole
(6) 1-(2,3-Dichlorophenyl-diphenyl)-methyl-imidazole
(7) 1-(2,6-Dichlorophenyl-diphenyl)-methyl-imidazole
(8) 1-(2-Methylphenyl-2'-methylphenyl-phenyl)-methyl-imidazole
(9) 1-(2-Chlorophenyl-2'-chlorophenyl-phenyl)-methyl-imidazole The new compounds of the formula I are also obtainable in an excellent manner according to the processes of Belgian Pat. Nos. 763,528, 754,670, 754,501 and 754,506 (identical reaction conditions).

The compounds according to the present invention exhibit good activity against dermatophytes, epidermatophytes and blastomyces and against biphase fungi and molds, for example Penicillium and Aspergillus. They can therefore be used with good success against fungal infections in man and animals.

The present invention includes pharmaceutical compositions which, in addition to pharmaceutically acceptable, nontoxic, inert excipients, comprise one or more compounds of the formula I and/or a pharmaceutically acceptable nontoxic salt thereof, as well as processes for the manufacture of these preparations.

The present invention also includes pharmaceutical preparations in dosage units. This means that the preparations are in the form of individual parts, for example tablets, dragees, capsules, pills, suppositories and ampoules, of which the active compound content corresponds to a fraction or a multiple of a single dose. The dosage units can, for example, contain 1, 2, 3 or 4 single doses or ½, ⅓ or ¼ of a single dose. A single dose preferably contains the amount of active compound which is given in one administration and which usually corresponds to a whole, half or one third or one quarter of a daily dose.

By pharmaceutically acceptable, nontoxic, inert excipients there are to be understood solid, semi-solid or liquid diluents, fillers and formulation auxiliaries of all kinds. Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds in addition to the customary excipients, such as (a) fillers and extenders, for example starches, lactose, sucrose, glucose, or mannitol and silica, (b) binders, for example carboxymethylcellulose, alginates, gelatine and polyvinyl pyrrolidone, (c) humectants, for example glycerine, (d) disintegrating agents, for example agar-agar, calcium carbonate and sodium carbonate, (e) solution retarders, for example paraffin and (f) resorption accelerators, for example quaternary ammonium compounds, (g) wetting agents, for example cetyl alcohol and glycerine monostearate, (h) adsorbents, for example kaolin and bentonite and (i) lubricants, for example talc, calcium stearate and magnesium stearate and solid polyethylene glycols, or mixtures of the compounds listed under (a)–(i).

The tablets, dragees, capsules, pills and granules can be provided with the customary coatings and shells which optionally contain opacifying agents and can also be so composed that they release the active compound or active compounds only, or preferentially, in a certain part of the intestinal tract and do so delayed, if desired, for which purposes it is possible to use, for example, polymeric substances and waxes as embedding compositions.

The compounds of the present invention can optionally also be in a micro-encapsulated form, optionally together with one or more of the above-mentioned excipients.

Suppositories can contain, in addition to the active compound or compounds, the customary water-soluble or water-insoluble excipients, for example polyethylene glycols, fats, for example cacoa fat and higher esters (for example $C_{14}$-alcohol with $C_{16}$-fatty acid) or mixtures of these compounds.

Ointments, pastes, creams and gels can contain the customary excipients in addition to the active compound or active compounds, for example animal and vegetable fats, waxes, paraffins, starch, tragacanth, cellulose derivatives, polyethylene glycols, silicones, bentonites, silica, talc and zinc oxide or mixtures of these compounds.

Powders and sprays can contain the customary excipients in addition to the compound of the present invention, for example lactose, talc, silica, aluminum hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or active compounds, such as solvents, solubilizing agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitane or mixtures of these substances.

For parenteral administration, the solutions and emulsions can also be in a sterile form which is isotonic with blood.

Suspension can contain, in addition to the compound of the present invention, the customary excipients such as liquid diluents, for example water, ethyl alcohol and propylene glycol, suspending agents, for example ethoxylated isostearyl alcohols, polyoxyethylene sorbitol and sorbitane esters, micro-crystalline cellulose, aluminum metahydroxide, bentonite, agar-agar and tragacanth or mixtures of these substances.

The formulations mentioned can also contain dyestuffs, preservatives and additives which improve the odor and flavor, for example peppermint oil and eucalyptus oil, and sweeteners, for example saccharin.

The compounds of the present invention should preferably be present in the above-mentioned pharmaceutical compositions in a concentration of about 0.1 to 99.5 percent, preferably about 0.5 to 95 percent, by weight of the total mixture.

The above-mentioned pharmaceutical compositions can also contain other pharmaceutically active compounds in addition to compounds of the formula I and/or their salts.

The above-mentioned pharmaceutical compositions are manufactured in the customary manner in accordance with known methods, for example by mixing the active compounds or active compounds with the excipient of excipients.

The present invention also includes the use of the compounds of the formula I and/or their pharmaceutically acceptable, nontoxic salt and of pharmaceutical compositions which contain one or more compounds of the formula I and/or their salts, in human and veterinary medicine, for the prevention, amelioration and/or healing of the above-mentioned illnesses.

The compounds of the present invention and the pharmaceutical compositions can be applied orally, parenterally, intraperitoneally, rectally and/or topically, preferably orally or topically.

In general it has proved advantageous, both in human medicine and in veterinary medicine, to administer the compound of the present invention in amounts of about 30 to 200 mg/kg, preferably 50 to 100 mg/kg, of body weight per 24 hours, optionally in the form of several separate adminisrations, in order to achieve the desired results. It may, however, be necessary to deviate from the dosages mentioned and, in particular, to do so as a function of the nature and severity of the infection, the patient's medical history, the nature of the composition and the administration thereof, as well as the time or interval within which the administration takes place. Thus, it can in some cases suffice to manage with less than the above-mentioned amount of the compound while in other cases the above-mentioned amount of the compound must be exceeded. The optimum dosage and route of administration for any particular type of treatment will be determined by evaluation of all of the above factors.

The good microbiological activity of the compounds according to the present invention can be seen from the following in vitro and in vivo experiments.

Determination of the antimycotic spectrum of activity in vitro by the series dilution test.

DESCRIPTION OF THE EXPERIMENT

The nutrient media used were Sabouraud's milieu d'epreuve for dermatophyties and molds and meat broth-glucose bouillon for blastomyces and biphase fungi.

The incubation temperature was 28° C and the incubation time was 24 to 96 hours.

The experimental results are summarized in Table A.

TABLE A

Minimum Inhibitory Concentration Values in γ/ml of Nutrient Medium

| Example No. (from Table 1) | Trichophyton mentagrophytes | | Candida Albicans | | Penicillium commune | Aspergillus niger | | Microsporon canis |
|---|---|---|---|---|---|---|---|---|
| | w.s. | n.s. | w.s. | n.s. | | w.s. | n.s. | |
| 1 | 4 | <1 | 10* | 1 | <1 | 40 | 4 | 4 |
| 2 | 10 | <1 | 10* | 1 | 100 | 4 | 1 | 4 |
| 3 | 40 | <1 | 10* | 1 | 4 | 40 | 1 | 4 |
| 4 | 10 | <1 | 40 | 1 | 4 | 10 | 1 | 4 |
| 6 | 4 | <1 | 4* | 1 | 4 | 10 | <1 | <1 |
| 7 | 4 | <1 | 10* | 1 | 4 | 4 | <1 | <1 |
| 8 | 10 | <1 | 10 | 1 | 10 | 10 | <1 | 4 |
| 9 | 4 | <1 | 4* | 1 | 1 | 10 | <1 | <1 |

Notes on Table A:
w.s. = with 30% serum added
n.s. = no added serum
* = 50% inhibition of growth Antimycotic action of the compounds of the formula I, according to the invention, in animal experiments.

(a) Topical application in experimental trichophytosis of guinea pigs (excitant: Trichophyton mentagrophytes)

Description of the experiment:

A 1% strength solution of the active compound in a dimethylsulphoxide/glycerine/water mixure (1:3:6) or in polyethylene glycol 400 was applied topically for 11 to 14 days after the trichophytosis had been caused experimentally.

The experimental results are reproduced in Table B.

TABLE B

Action of the Compounds of the Formula I, According to the Invention, in Trichophytosis of Guinea Pigs

| Example No. (from Table 1) | Trichophyton mentagrophytes |
|---|---|
| 2 | ++++ |
| 3 | +++ |
| 4 | ++ |
| 6 | ++ |
| 7 | +++ |
| 8 | ++ |
| 9 | +++ |

++ = slight action = reduction of symptoms of the infection
+++ = action = rapid healing of the infection
++++ = good action − complete suppression of symptoms of the infection (b) Action of oral administration on *Quinckeanum trichophytosis* in white mice.

With doses of 50, 75 and 100 mg/kg administered orally once daily up to the eighth day of infection, it was possible to suppress the development of the Quinckeanum infection in mice. In the case of preparations with a "good action" from experiment a) (Table B), 0–1 out of 20 of the treated mice showed scutula, which are to be regarded as a typical sign of infection of *Quinckeanum trichophytosis*, 10 days after infection, while in the untreated control 19 out of 20 mice showed these.

(c) *Candidosis* in mice

Description of the experiment:

Mice of the type SPF-$C_1$ were infected intravenously with 1–2 × $10^6$ logarithmically-growing Candida cells suspended in physiological sodium chloride solution.

One hour before, and 7 hours after, the infection the animals are treated orally with 50, 75, 100 and 150 mg/kg of body weight of the preparations.

Untreated animals died of the infection 3 to 6 days after infection. The survival rate on the 6th day after infection was ~ 5% in untreated control animals.

The experimental results are summarized in Table D.

TABLE D

Action on candidosis in Mice

| Example No. (from Table 1) | Candida albicans |
|---|---|
| 1 | +++++ |
| 2 | +++++ |
| 3 | ++++ |
| 4 | +++++ |
| 6 | +++++ |
| 7 | +++++ |
| 8 | +++++ |
| 9 | ++++ |

Explanation of symbols:
++++ = good action = >80% survival on the 6th day after infection
+++++ = very good action = >90% survival on the 6th day after infection The following nonlimitative examples more particularly illustrate the present invention.

EXAMPLE 1

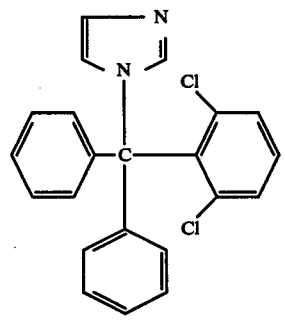

31.2 g (0.1 mol) of 1-(2,6-dichlorophenyl-diphenyl)-methyl chloride are dissolved in 200 ml of anhydrous acetonitrile, 13.6 g (0.2 mol) of imidazole are added and the mixture is heated to the boil under reflux for 2½ hours. Thereafter the solvent is distilled off in vacuo. The brown, oily residue thus obtained is washed with water and thereafter taken up in ether, and the ether solution is dried over sodium sulphate and filtered. Dry hydrogen chloride gas is slowly passed into the ether solution and the hydrochloride which has precipitated is rapidly filtered off and taken up in methylene chloride. This solution is treated with a 30% strength sodium carbonate solution while stirring, the organic phase is separated off and dried and the solvent is distilled. The residue is recrystallized from a little acetonitrile.

Approximately 6 g (approximately 16% of theory; yield of purified material) of 1-(2,6-dichlorophenyl-diphenyl)-methyl-imidazole of melting point 168° C are obtained.

The 1-(2,6-dichlorophenyl-diphenyl)-methyl chloride used as the starting product is manufactured as follows:

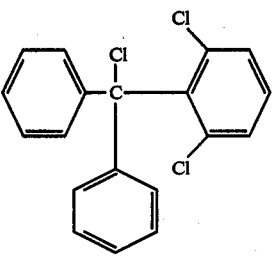

A solution of 21.4 g (0.2 mol) of bromobenzene in 100 ml of anhydrous ether is added dropwise to a suspension of 4.8 g (0.2 mol) of magnesium filings in 50 ml of anhydrous ether. When the magnesium has dissolved, 200 ml of an ether solution, which contains 37.5 g (0.15 mol) of 2,6-dichlorobenzophenone, are slowly added dropwise at room temperature and the reaction mixture is stirred overnight. Thereafter it is hydrolyzed with an ice-hydrochloric acid mixture and the organic phase is separated off. The aqueous phase is extracted twice more with 100 ml of ether at a time and the combined organic phases are dried over sodium sulphate. After distilling off the solvent in vacuo, a yellowish crude oil remains, which is repeatedly extracted with cold pentane for further purification. After distilling off the pentane, a mass which is difficult to crystallize is obtained and this is taken up in 200 ml of methylene chloride and reacted with 23.6 g (0.2 mol) of thionyl chloride at 10° C using a reaction time of half an hour.

The remaining trityl halides which can be used as starting materials are also obtainable in an analogous manner (same reaction conditions and solvents).

EXAMPLE 2

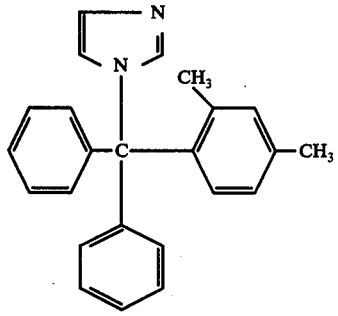

30.6 g (0.1 mol) of 1-(2,4-dimethylphenyl-diphenyl)-methyl chloride are dissolved in 200 ml of anhydrous acetonitrile and heated to the boil with 13.6 g (0.2 mol) of imidazole for 2 hours under reflux. After distilling off the solvent in vacuo, the oily residue is well washed with distilled water and recrystallized from a little acetonitrile. 15.9 g (47% of theory; yield of purified material) of 1-(2,4-dimethyl-phenyl-diphenyl)-methyl-imidazole of melting point 168°-169° C are thus obtained.

The compounds listed in Table 2 are produced analogously to Examples 1 and 2 (same reaction conditions and solvents).

TABLE 2

| Example No. | X | Z | Y | Melting Point, °C |
|---|---|---|---|---|
| 3 | CH₃ | 3-CH₃ | H | 129 |
| 4 | CH₃ | 5-CH₃ | H | 119 |

TABLE 2-continued

| Example No. | X | Z | Y | Melting Point, °C |
|---|---|---|---|---|
| 5 | CH$_3$ | 4-Cl | H | 188 |
| 6 | Cl | 3-Cl | H | 128 |
| 7 | CH$_3$ | H | CH$_3$ | 161 |
| 8 | Cl | H | Cl | 180 |

EXAMPLE 3

In a manner analogous to that of Examples 1 and 2, 1-(2-chloro-4-methylphenyl-diphenyl)-methyl-imidazole is produced.

What is claimed is:

1. A pharmaceutical composition for treating mycotic infections in humans and animals which comprises an anti-mycotically effective amount of 1-(2,6-dichlorophenyl-diphenyl)-methyl-imidazole or a pharmaceutically acceptable non-toxic salt thereof, in combination with a pharmaceutically acceptable non-toxic inert carrier.

2. A pharmaceutical composition for treating mycotic infections in humans and animals which comprises an anti-mycotically effective amount of 1-(2,3-dichlorophenyl-diphenyl)-methyl-imidazole or a pharmaceutically acceptable non-toxic salt thereof, in combination with a pharmaceutically acceptable non-toxic inert carrier.

3. A pharmaceutical composition for treating mycotic infections in humans and animals which comprises an anti-mycotically effective amount of 1-(2-chlorophenyl-2'-chlorophenyl)-methyl-imidazole or a pharmaceutically acceptable non-toxic salt thereof, in combination with a pharmaceutically acceptable non-toxic inert carrier.

4. A method of treating mycotic infections in humans and animals which comprises administering to a human or animal in need thereof an anti-mycotically effective amount of 1-(2,6-dichlorophenyl-diphenyl)-methyl-imidazole or a pharmaceutically acceptable non-toxic salt thereof, in combination with a pharmaceutically acceptable non-toxic inert carrier.

5. A method of treating mycotic infections in humans and animals which comprises administering to a human or animal in need thereof an anti-mycotically effective amount of 1-(2,3-dichlorophenyl-diphenyl)-methyl-imidazole or a pharmaceutically acceptable non-toxic salt thereof, in combination with a pharmaceutically acceptable non-toxic inert carrier.

6. A method of treating mycotic infections in humans and animals which comprises administering to a human or animal in need thereof an anti-mycotically effective amount of 1-(2-chlorophenyl-2'-chlorophenyl)-methyl-imidazole or a pharmaceutically acceptable non-toxic salt thereof, in combination with a pharmaceutically acceptable non-toxic inert carrier.

* * * * *